United States Patent [19]

Hammerslag et al.

[11] Patent Number: 5,037,391
[45] Date of Patent: Aug. 6, 1991

[54] STEERABLE ANGIOPLASTY DEVICE

[75] Inventors: Julius G. Hammerslag, San Juan Capistrano; Gary R. Hammerslag, Dana Point, both of Calif.

[73] Assignee: Pilot Cardiovascular Systems, Inc., San Clemente, Calif.

[21] Appl. No.: 562,455

[22] Filed: Aug. 1, 1990

Related U.S. Application Data

[63] Continuation of Ser. No. 489,706, Mar. 7, 1990, abandoned, which is a continuation of Ser. No. 295,124, Jan. 9, 1989, Pat. No. 4,921,482.

[51] Int. Cl.[5] .............................................. A61M 37/00
[52] U.S. Cl. ..................................... 604/95; 604/164; 128/772
[58] Field of Search .......... 604/95, 164, 170, 280–282; 128/657, 772

[56] References Cited

U.S. PATENT DOCUMENTS

| Re. 33,166 | 2/1990 | Samson | 128/772 |
|---|---|---|---|
| 3,470,876 | 10/1969 | Barchilon . | |
| 3,547,103 | 12/1970 | Cook . | |
| 3,605,725 | 9/1971 | Bentov . | |
| 3,757,768 | 9/1973 | Kline . | |
| 3,773,034 | 11/1973 | Burns et al. . | |
| 4,456,017 | 6/1984 | Miles | 604/95 X |
| 4,538,622 | 9/1985 | Samson et al. | 604/95 X |
| 4,543,090 | 9/1985 | McCoy | 604/95 |
| 4,545,390 | 10/1985 | Leary | 604/95 |
| 4,554,929 | 11/1985 | Samson et al. | 604/95 X |
| 4,581,017 | 4/1986 | Sabota | 604/101 |
| 4,582,181 | 4/1986 | Samson | 604/95 X |
| 4,616,653 | 10/1986 | Samson et al. | 604/95 X |
| 4,641,654 | 2/1987 | Samson et al. | 604/95 X |
| 4,650,466 | 3/1987 | Luther | 604/95 |
| 4,654,024 | 3/1987 | Crittenden et al. | 604/49 |
| 4,676,249 | 6/1987 | Arenas et al. | 604/164 X |
| 4,719,924 | 1/1988 | Crittenden et al. | 128/772 |
| 4,721,117 | 1/1988 | Mar et al. | 128/772 |
| 4,723,936 | 2/1988 | Buchbinder et al. | 604/95 |
| 4,724,846 | 2/1988 | Evans | 128/772 |
| 4,726,369 | 2/1988 | Mar | 604/101 X |
| 4,748,981 | 6/1988 | Crittenden | 604/101 X |
| 4,748,982 | 6/1988 | Horzewaki et al. | 604/102 X |
| 4,757,827 | 7/1988 | Buchbinder et al. | 128/772 |
| 4,758,222 | 7/1988 | McCoy | 604/95 |
| 4,763,647 | 8/1988 | Gambale | 128/772 X |
| 4,775,371 | 10/1988 | Mueller, Jr. | 604/280 |
| 4,798,598 | 1/1989 | Bonello et al. | 604/280 |
| 4,813,434 | 3/1989 | Buchbinder et al. | 128/772 |
| 4,815,478 | 3/1989 | Buchbinder et al. | 128/772 |
| 4,820,349 | 4/1989 | Saab | 604/101 X |
| 4,827,941 | 5/1989 | Taylor et al. | 128/772 X |
| 4,832,047 | 5/1989 | Sepetka et al. | 128/772 |
| 4,846,186 | 7/1989 | Box et al. | 128/772 X |
| 4,846,193 | 7/1989 | Tremulis et al. | 128/772 |
| 4,850,351 | 7/1989 | Herman et al. | 604/21 X |
| 4,875,481 | 10/1989 | Higgins | 604/96 X |
| 4,875,489 | 10/1989 | Messner et al. | 128/772 |
| 4,877,031 | 10/1989 | Conway et al. | 604/96 X |
| 4,886,067 | 12/1989 | Palermo | 128/772 X |
| 4,892,519 | 1/1990 | Songer et al. | 604/96 |

FOREIGN PATENT DOCUMENTS 193885 1/1965 Sweden .

*Primary Examiner*—John D. Yasko
*Attorney, Agent, or Firm*—Knobbe, Martens, Olson & Bear

[57] ABSTRACT

An elongate steerable implement is disclosed, which may be either a steerable guidewire or catheter for coronary angioplasty applications. A floppy steerable tip on a steering region at the distal end of the implement and a control device at the proximal end are connected by means of a plurality of axially movable deflection wires extending throughout the implement. Manipulation of the control permits deflection of the steering region throughout a full 360° range of motion about the axis of the implement, without axial rotation or "torquing" thereof.

22 Claims, 2 Drawing Sheets

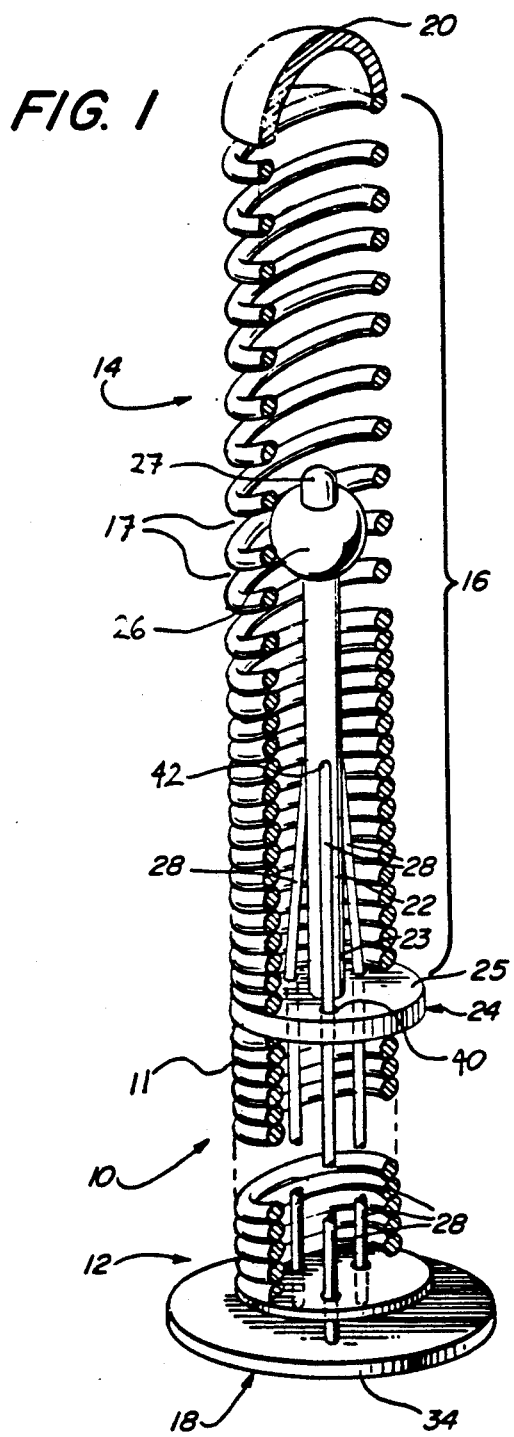
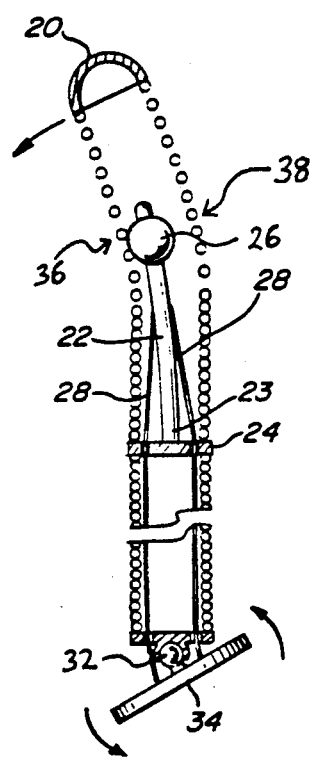
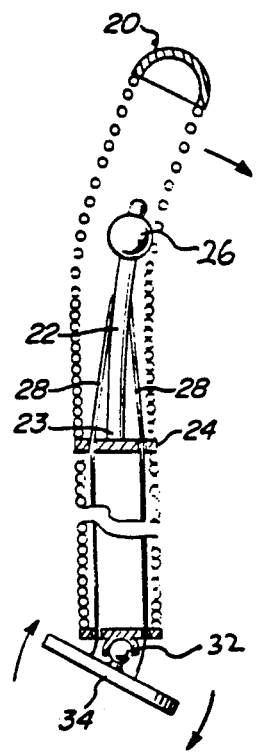
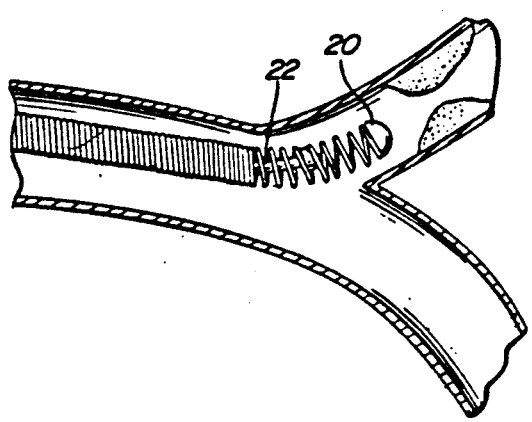

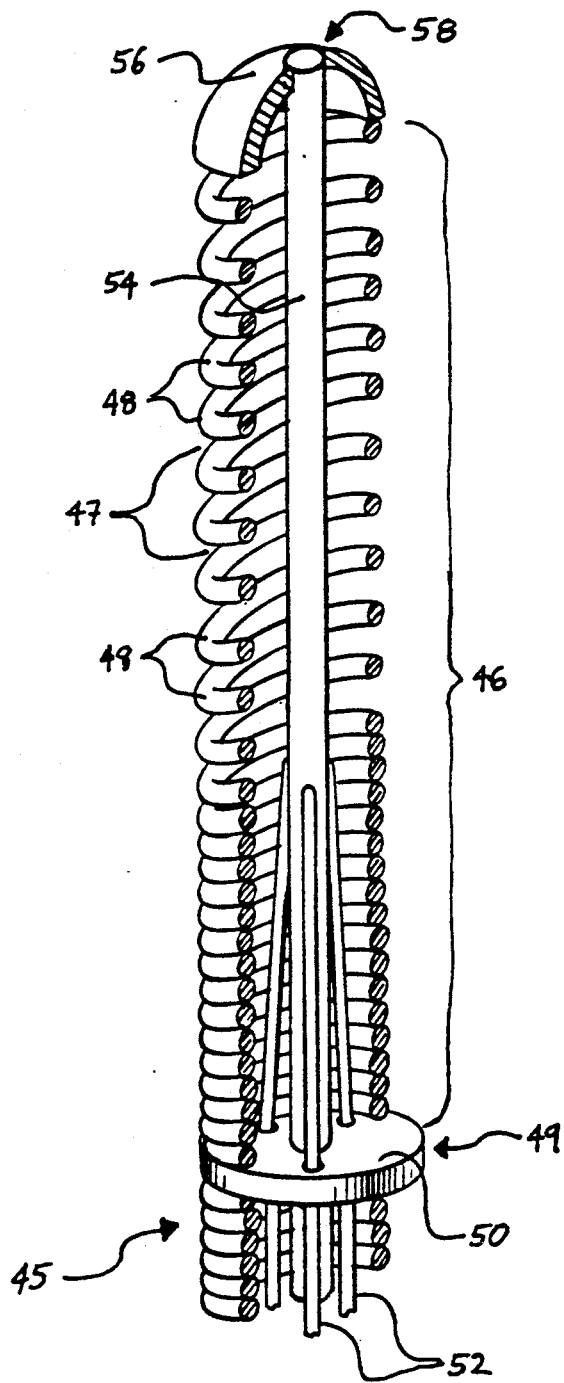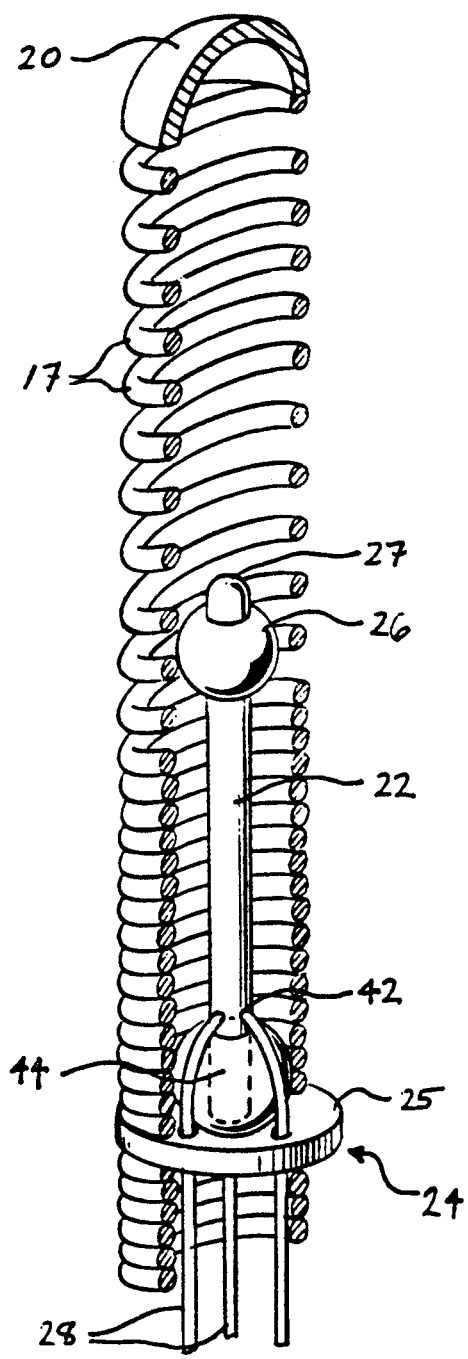

STEERABLE ANGIOPLASTY DEVICE

This application is a continuation of application Ser. No. 489,706, filed Mar. 7, 1990, now abandoned which is a continuation of Ser. No. 295,124, filed Jan. 9, 1989, now U.S. Pat. No. 4,921,482.

BACKGROUND OF THE INVENTION

The present invention relates to steering devices such as may be used with catheters, cannulae, guidewires and the like. More particularly, the present invention relates to catheters and guidewires that are steerable through body lumen or cavities and positionable within or aimable at obstructions, organs, or tissue within the body from a position external to the body.

Medical catheters generally comprise elongate tubelike members which may be inserted into the body, either percutaneously or via a body orifice, for any of a wide variety of diagnostic and therapeutic purposes. Such medical applications frequently require use of a catheter having the ability to negotiate twists and turns, particularly with regard to certain cardiovascular applications.

One such application, Percutaneous Transluminal Coronary Angioplasty (balloon angioplasty), requires manipulation of a catheter from a position outside the patient's body through extended portions of the patient's arterial system to the stenotic site for the purpose of alleviating the obstruction by inflating a balloon. This particular procedure has been performed with increasing frequency over the past years in preference to open heart bypass surgery, when possible.

In a typical angioplasty procedure, a guidewire is transluminally inserted into the brachial or the femoral artery, to be positioned within the stenotic region and followed by a balloon catheter. The cardiologist usually prebends the distal tip of the guidewire before insertion and then rotates (or torques) the wire once it has reached a branch artery to enable the guidewire to enter the branch. If the angle of the bend has to be adjusted, the guidewire must be removed, re-bent and reinserted, sometimes several times. Particular difficulty is encountered with prebending where an artery branches at one angle, and then sub-branches at a different angle. This procedure is attended by the risk of significant trauma to the arterial lining, and, in many cases, the obstruction cannot be reached at all with the guidewire and catheter.

Coronary arteries are tortuous, have many sub-branches and often the obstruction is either located where the diameter of the artery is small or, by its very presence, the obstruction leaves only a very small opening through which a guidewire and/or catheter can be passed. Consequently, the cardiologist often finds it very difficult to maneuver the guidewire or catheter, which are typically several feet long, from the proximal end.

Steering the prebended guidewire is further complicated by the fact that branches project at all different radial angles, thus necessitating rotation of the guidewire to the appropriate degree to enter the desired arterial branch. However, rotation of the distal end of the wire typically lags behind rotation of the proximal control end, so that precise rotational control is not possible. Also, friction in the arteries can cause the distal end to rotate in a jerky fashion which can traumatize the vascular intima.

In another application, Transluminal Laser Catheter Angioplasty (laser angioplasty), the delivery of laser energy from an external source to an intraluminal site to remove plaque or thrombus obstructions in vessels is accomplished by providing a waveguide such as a fiber optic bundle within a catheter. The nature of laser angioplasty requires an even greater ability to precisely manipulate the catheter, to control and aim the laser light at the specific plaques or thrombi to be removed.

A variety of attempts have been made in the past to provide catheters which are steerable from the proximal end to enable the catheter to be aimed or advanced through nonlinear body cavities. For example, U.S. Pat. No. 4,723,936 to Buchbinder, et al. discloses a balloon catheter, which is said to be steerable from the proximal end. The catheter is provided with a deflection wire going along the entire length of the catheter, which may be axially displaced to cause deflection at the distal end. However, the tip of the catheter can be bent in one direction only, and the entire catheter must be rotated or torqued to be guided. In addition, the design requires a relatively large diameter deflection wire, which precludes extremely thin diameter catheters, such as those preferred for use for laser or balloon angioplasty applications.

U.S. Pat. No. 3,470,876 to Barchilon discloses a catheter device having a central lumen extending therethrough, and four tensioning cords extending along an inner wall of the catheter. The '876 patent specifically recites that catheters may be produced in accordance with the Barchilon design having diameters of 0.125 to 2 inches, and are suited for applications such as within the duodenal bulb or ascending colon. These diameters are unsuited for use as a guidewire in coronary angioplasty, which typically requires diameters in the area of as small as from about 0.014 to 0.018 inches.

In the context of coronary angioplasty applications, the prior art generally suffers from disadvantages such as limited steerability and excessive external diameters. Limited catheter tip steerability results in greater time spent in the body and significantly elevated risk of trauma both to the vascular intima and to the patient in general. Multiple insertions of guidewires or catheters may lead to thrombosis, as a result of coagulation commencing along a guidewire surface. Additionally, precise directional control in laser angioplasty is of the utmost importance to assure accurate aiming of the laser beam to ablate the attendant plaque. However, the only prior art catheters having multi-directional steerability are typically greatly in excess of practical angioplasty catheter diameters.

Thus, there remains a need for a small diameter steering device, which may be readily adapted for use in the construction of either guidewires or catheters, and which is especially suited for procedures such as balloon or laser angioplasty. Preferably, the steering device is constructed in a manner which permits a diameter as small as that of existing dilatation catheters or guidewires used in angioplasty applications, yet is capable of complete deflective movement, throughout a full 360° range of motion, without axial rotation.

SUMMARY OF THE INVENTION

In accordance with one aspect of the present invention, there is provided an improved steerable guidewire or catheter implement of the type useful for percutaneous transluminal insertion into the coronary vascular system. The invention permits controlled negotiation of branches and turns to guide an angioplasty catheter or guidewire to an arterial stenosis or lesion or other treatment site without the need for prebending or torquing of the instrument. The distal tip on steerable implements made in accordance with the present invention can be controllably radially displaced in any direction, thus permitting a full 360° range of motion without the need to rotate the body of the steerable implement.

In one embodiment of the present invention, a guidewire is provided having an elongate flexible shaft with a central lumen extending therethrough and a floppy resilient tip on the distal end. An axially extending steering post is disposed within a steering region on the distal portion of the flexible shaft. The steering post is pivotably secured at its proximal end to a radial support axially secured within the flexible shaft at the proximal end of the steering region, to prevent axial displacement of the steering post while at the same time permitting lateral deflection of the steering post out of parallel with the axis of the flexible shaft.

At least one and preferably four deflection wires are axially movably disposed within the lumen of the flexible shaft, and extend proximally from distal point of attachment on the steering post throughout the length of the flexible shaft to a control at the proximal end thereof. Each deflection wire passes through a notch or orifice on the radial support.

Axial movement of any one of the deflection wires in a proximal direction displaces the axis of the steering post in a unique lateral direction, and through combinations of proximal axial displacement of more than two deflection wires, the steering post is caused to deflect laterally and rotate throughout a full 360° range of motion about the axis of the flexible shaft.

The steerable angioplasty device of the present invention can thus negotiate tortuous and branched arterial systems, without the need for withdrawal and multiple insertions to deflect the tip, or axial rotation of the catheter body. The steerable angioplasty device can be readily manufactured in accordance with known techniques, and at a low per unit cost.

These and other features and advantages of the present invention will become apparent from the detailed description of preferred embodiments which follows, when considered together with the attached drawings and claims.

BRIEF DESCRIPTION OF THE DRAWINGS

FIG. 1 is a partial sectional perspective view of a steerable guidewire according to the present invention, with the outer tubular casing removed.

FIG. 2 is an elevational sectional view of the guidewire of FIG. 1, illustrated in a first deflected position.

FIG. 3 is an elevational sectional view of the guidewire of FIG. 1, illustrated in a second deflected position.

FIG. 4 is a partial sectional perspective view of a steerable laser angioplasty catheter according to the present invention.

FIG. 5 is a further embodiment of the steerable guidewire of the present invention.

FIG. 6 is a schematic view of the guidewire of FIG. 1, illustrated as negotiating an arterial branch point and approaching an arterial stenosis.

DETAILED DESCRIPTION OF PREFERRED EMBODIMENTS

Referring to FIG. 1, there is disclosed an elongate flexible implement 10, having a tubular body with a proximal end 12 and a distal end 14. The distal end 14 comprises a steering region 16, and the proximal end 12 is provided with a control 18 for steering the implement 10, which may be, for example, a steerable guidewire or catheter. Although the steering device of the present invention will generally be described herein as incorporated into an angioplasty guidewire, it is to be understood that one skilled in the art will be able to readily adapt the steering device to other medical and nonmedical applications.

The body 11 of steerable implement 10 may be any desired length from inches to many feet depending upon the intended application. In an embodiment useful as an angioplasty guidewire or catheter, the body 11 will typically be several feet long, and will preferably be about 180 cm, as is typical of existing angioplasty catheters. However, any suitable length may be used.

The body 11 may be constructed in any of a variety of ways known in the art, such as by tightly winding a coil of metal wire, or extrusion of a relatively flexible biocompatible polymer such as polyethylene. Wound guidewires preferably comprise a high tensile strength wire of a resilient, noncorrosive metal such as stainless steel or platinum, and may have a circular cross-section with a diameter of from about 0.001 to 0.020 in. The wire may alternatively have a rectangular cross-section of from about 0.001 to 0.020 inches by from about 0.001 to 0.040 inches, or other variations known in the art. Construction materials and techniques for manufacturing wire wound guidewires are well known in the art, and a typical 180 cm teflon coated 0.014 inch or 0.016 inch diameter nonsteerable guidewire may be obtained from U.S. Catheter, Inc., a division of C. R. Baid, Inc., located in Billeriea, Massachusetts, U.S.A.

The external diameter of wire wound guidewires will of course be a function of the intended application. The wire wound coronary angioplasty guidewires incorporating the steering device of the present invention are preferably wound to have an external diameter in the range of from about 0.014 inches to about 0.018 inches. In steerable catheter applications, the diameter of the catheter can be varied to optimize the diameter of a central working channel as desired, while still maintaining a sufficiently small exterior diameter for the intended application. Steerable balloon angioplasty catheters incorporating the present invention will typically have an exterior diameter in the range of from about 0.020 inches to about 0.041 inches or larger as permitted by location of the lesion.

Preferably, the exterior surface of the wound coil type guidewire shaft 10 is provided with an elastic, biocompatible coating or sheath to provide a smooth outer surface. Suitable coatings can be formed by dipping, spraying or wrapping and heat curing operations as are known in the art. Alternatively, heat shrinkable tubing can provide a suitable outer sheath. A coating material should be selected which will permit sufficient flexing of the body without cracking, will minimize sliding friction of the implement 10 during insertion and removal, and is substantially chemically inert in the in vivo vascular environment. A variety of suitable materials are known, including, for example, polytetrafluoroethylene, urethane or polyethylene.

The body of flexible implement 10 typically terminates at its distal end 14 in a closed tip 20. Numerous guidewire and catheter tip constructions are known in the art and need not be detailed extensively herein. In general, the tip 20 is preferably a rounded closure constructed of a resilient polymeric material such as silicone or urethane which will minimize trauma to the vascular intima, as will be appreciated by one of skill in the art. As a safety feature, to facilitate complete removal of fragments of a broken guidewire, a safety wire may be secured at one end to the inside of the tip 20, and at the other end to the post 22 or support 24.

Disposed intermediate the tip 20 and body 11 of a flexible implement 10 in accordance with the present invention is a floppy but controllable steering region 16. Steering region 16 is constructed in a manner that facilitates lateral displacement of the tip 20 relative to the axis of the body 11, through physical design and/or choice of flexible construction materials.

For example, in a typical angioplasty guidewire or catheter, where the flexible body 11 comprises a metal wire coil, the revolutions of wire per unit of axial distance along the body is reduced in the steering region 16 relative to body 11 to provide a looser wound coil having space 17 between adjacent wire loops, as illustrated in FIGS. 1-6. Thus, referring to FIG. 2, it can be seen that lateral deflection of steering region 16 to the left may involve both an axial compression of adjacent wire loops on the inside surface 36 of the bend, and an axial separation of the adjacent wire loops on the outside surface 38 of the bend.

Alternative designs or materials can be employed, provided that the catheter exhibits sufficient lateral flexibility. In general, the steering region 16 may be made from a variety of suitable metal or plastic coils or flexible sleeves. Materials opaque to X-rays, such as platinum, gold, tungsten, tantalum or the like, may be advantageously incorporated therein, to act as a fluoroscopic marker to aid in precise positioning of a balloon section of the catheter.

In accordance with the steering mechanism of the present invention, a steering post 22 is provided, extending in a generally axial direction within the steering region 16 of flexible body 11. Preferably, the steering post 22 is disposed coaxially within the central lumen of steering region 16 when the steering region 16 and body 11 are linearly aligned, such as when at rest. See FIG. 1. As will be described, the steering post 22 is secured in the steering region 16 in a manner that substantially prevents axial displacement thereof yet permits lateral deflection of the axis of the steering post 22 away from the axis of body 11.

Post 22 preferably comprises a resilient shaft which may be molded or extruded from any of a variety of materials, such as nylon, and may have a cross-sectional dimension of from about 0.002 inches up to about 0.012 inches for use in a typical steerable angioplasty guidewire embodiment. Alternatively, a variety of resilient or springy metals in the form of wire can also be used to form post 22, such as phosphor bronze or other resilient metal. In general, it is desirable to select a material which will permit some degree of bending and return to its original shape, and will resist axial compression under the forces typically applied in the intended use of the steerable implement 10.

The length of steering post 22 will, of course, be dependant upon the length of the steering region 16. In a typical steerable guidewire for angioplasty applications, the entire steering region 16 will be on the order of from about 0.25 to about 1.0 inches long, and the steering post 22 may be from one-third to two-thirds that length. Although steering post 22 may extend distally all the way to the distal tip 20 of the steerable implement 10, it is preferred to limit the length to the proximal one-half or one-third of the axial length of steering region 16 to minimize rigidity in the steering region 16 yet permit sufficient steerability thereof.

For example, in a typical angioplasty guidewire the distal end 27 of steering post 22 will be spaced apart from the interior surface of tip 20 by a distance of from about one-tenth to one-half an inch or more, thus permitting the steering region 16 of the catheter shaft to be as floppy as desired. However, in an embodiment where the distal portion of a fiber optics bundle or flexible tube for defining a working channel additionally functions as the steering post 22, the post 22 will extend all the way to the distal tip 20 and be exposed to the outside by way of an opening therethrough. See, for example, FIG. 4.

In a particularly preferred embodiment, steering post 22 is further provided with a bead or enlarged region 26 to optimize transmission of lateral force from the steering post 22 to the wall of steering region 16. For this purpose, bead 26 is most effectively located at or near the distal end of steering post 22. Bead 26 may be formed by dipping or coating techniques, or may be a preformed member having an opening therein for sliding over the end of steering post 22. Alternatively, post 22 can be molded or milled to provide a bead 26 integrally formed thereon. Bead 26 is preferably substantially circular in a cross-section perpendicular to the axis of post 22, and the external diameter of the bead 26 is only slightly less than the interior diameter of the steering region 16 so that maximum lateral motion of the steering post 22 is transmitted to the steering region 16, but bead 26 also remains only in slidable contact with the interior surface thereof.

The proximal end 23 of the steering post 22 is mounted to or in pivotable contact with a radial support 24, in a manner which permits pivoting of the steering post 22 throughout a full 360° range of motion about the axis of body 11 The post may also be molded or milled as an integral part of disk 24. The support 24 comprises any means by which the deflection wires 28 are displaced radially outwardly from the axis of the tubular body 11, relative to their point of attachment to the steering post 22, as will be discussed.

Referring to FIG. 1, the support 24 of the illustrated embodiment comprises a circular disk 25 located within the tubular body 11 of the steerable implement 10, preferably located near the distal end thereof. The disk 25 is axially secured within the tubular body 11 to provide a stationary radial support for at least one deflection wire 28, and pivotable mount for steering post 22. Disk 25 may be attached, for example, by friction fit between adjacent turns of coiled spring wire. Steering post 22 preferably is attached to or in contact with the disk 25 in a manner which permits it to swivel from 90 degrees to close to 0 degrees, relative to the lateral plane of disk 25.

The disk 25 may be made of stainless steel or any of a variety of other suitable materials such as other metals or plastic polymers which will provide a sufficiently axially rigid seat for the proximal end 23 of steering post 22. Disk 25 may be formed by stamping from sheet stock and drilling, injection molding, or other techniques well known in the art. Preferably, a central depression or orifice is provided thereon, for providing an axial seat for steering post 22. The diameter of disk 25 can vary, however, it will typically be no greater than, but may approximate the outside diameter of the steerable implement 10. Diameters from about 0.14 to 0.050 inches may preferably be used in the construction of cardiac angioplasty catheters.

Lateral deflection of the steering post 22 away from the axis of body is accomplished by proximal axial displacement of any of a plurality of deflection wires 28 extending proximally throughout the length of flexible body 11. Although only a single deflection wire 28 or two deflection wires can be used, preferably three or four deflection wires 28 are employed to provide a full 360° range of motion of the steering region 16 about the axis of the body 11, as will become apparent. Only a single deflection wire 28 will be described in detail herein.

The distal end of deflection wire 28 is secured such as by adhesives to the steering post 22 at the distal end thereof, or at a variety of other locations along the length of post 22. Typically, securing deflection wire 28 closer to the proximal end 23 of post 22 will maximize the lateral force component generated by axial displacement of the deflection wire 28, and for that reason, deflection wire 28 is preferably secured to post 22 within the proximal half or one-third of the axial length of the post 22 extending distally of support 24. By "attached" or "secured" to the post and similar language herein, it is to be understood that the deflection wire 28 must be mechanically linked to the post 22 but need not necessarily be directly secured thereto. For example, the deflection wire 28 could be secured to an annular flange or ring surrounding the post or other structure which may be convenient from a manufacturing standpoint to provide a sufficiently secure linkage to accomplish the intended steering function. Alternatively, an eye on the end of the deflection wire can surround the post 22 and rest against a stop formed by a milled shoulder or adhesive, or other means of attachment as will be apparent to one of skill in the art.

The deflection wire 28 preferably extends radially outwardly from the point of attachment to the steering post 22 to the support 24. For this purpose, the support 24 is preferably provided with a notch or orifice 40 for each deflection wire 28 to extend through, said orifice 40 spaced radially outwardly from the axis of the tubular body 11 by a first distance. The distal end of each deflection wire 28 is secured to the steering post 22 at a point radially displaced from the axis of the steering post 22 by a second distance, and the first distance is preferably greater than the second distance to maximize the lateral component of force. The second distance preferably approaches zero; however, it will inherently include the radius of the steering post 22 where the deflection wire 28 is secured intermediate the two ends thereof.

In the most preferred embodiment of the present invention, four deflection wires 28 are provided, each passing through an orifice 40 in support 24 spaced at angles of approximately 90° apart from each other along the plane of the support 24. In a three deflection wire embodiment, as illustrated in FIG. 1, each orifice 40 is separated from each adjacent orifice by an angle of approximately 120°.

The deflection wires may be made of stainless steel, nylon or any other suitable material which provides sufficient tensile strength and flexibility. The diameter of the lines can range from 0.001 to 0.005 inches or more, and suitability of particular sizes or materials can be readily determined by experimentation.

A control device 18 for steering the catheter is shown schematically in FIGS. 1-3. The control device 18 is preferably provided at its center with a pivotable mount 32 to permit it to be tipped throughout a full 360° range of motion. In the illustrated embodiment, control comprises a circular plate 34 secured to proximal end 12 of flexible shaft 10 by way of pivotable mount 32. Deflection wires 28 are spaced equally radially outwardly from the pivotable center of the control device and at equal angular distances around the plate 34. Deflecting plate 34 from a plane normal to the axis of shaft 10 transmits force via one or more deflection wires 28, a component of which is resolved into a lateral force to deflect the catheter tip toward or away from the longitudinal axis of catheter. Selective tipping of the deflection plate 34 results in rotation of the catheter tip to any desired orientation.

A variety of alternative control devices can be envisioned for use with the steerable implement of the present invention. For example, a "joy stick" type device comprising a single lever which can be displaced to any position throughout a nearly hemispherical range of motion might be used. As a further alternative, a portion of the proximal end 12 of tubular body 11 is enlarged to a cross-section of a half inch or larger to facilitate grip. The enlarged section is provided with a plurality of axially slidable switches, one corresponding to each deflection wire 28. Manipulation of the switches by the thumb or forefinger will obtain the desired deflection of steering region 16. As will be appreciated by one of skill in the art, any control device will preferably be provided with a stop to prevent bending of the post 22 or steering region 16 past its elastic limit.

A variety of factors impact the amount of the lateral force component exerted on steering post 22 by axial, proximal displacement of any of deflection wires 28. For example, as orifice 40 is moved further in a radially outward direction, the lateral force component will increase. Lateral displacement of orifice 40, however, is constrained by the maximum diameter that the steerable implement can have for an intended application.

Alternatively, shortening the axial distance from the support 24 to the point of attachment 42 of the deflection wire 28 to the steering post 22 increases the angle between the axis of post 22 and deflection wire 28, thereby increasing the lateral component of force. For this reason, support 24 is typically within one or two inches, and preferably less than one inch, from the distal tip 20 of an angioplasty catheter or guidewire embodiment of the invention.

A further alternative is illustrated in FIG. 5. In this embodiment, a fulcrum 44 is provided at a point intermediate the radial support 24 and point of attachment 42 for maintaining the deflection wire 28 concave in a radial inward direction. The fulcrum 44 may conveniently comprise a substantially radially symmetrical member such as a sphere or toroid, which can also function to limit proximal axial movement of steering post 22 through a central opening in support 24. In this embodiment, the point of attachment of deflection wires 28 may be to the fulcrum 44 instead of directly to the steering post 22.

In accordance with a further aspect of the present invention, there is provided a steerable medical implement for use in percutaneous transluminal laser angioplasty applications. Referring to FIG. 4, there is disclosed an elongate flexible implement 45 comprising at its distal end a floppy steering region 46. As described with previous embodiments, enhanced flexibility may be imparted to steering region 46 by providing spacing 47 between adjacent loops of wound wire 48.

A radial support means 49 is disposed at the proximal end of steering region 46, which may comprise a circular plate 50 or other structure for displacing deflection wires 52 radially outwardly from the axis of implement 45.

A waveguide such as a fiber optic bundle 54 extends the entire length of the implement 45, for directing laser light from a source (not illustrated) disposed at the proximal end of the implement 45, to a point of application within a coronary artery at the distal tip 56 of the implement 45. For this purpose, the optical pathway 54 extends throughout the length of steering region 46 and traverses tip 56 by way of an opening 58 therein.

Each of the deflection wires 52 is secured at its distal end to the fiber optic bundle 54 at a point intermediate radial support 49 and distal tip 56. Preferably, as has been previously described, the point of attachment of deflection wires 52 to the fiber optic bundle 54 is less than half the distance and preferably is within one-third of the distance between the radial support 49 and distal tip 56, in order to optimize the lateral component of force.

Thus, utilizing a control device as previously described, a laser angioplasty catheter incorporating the present invention permits the controlled direction of a beam of light transmitted through fiber bundle 54 at any desired point within a full 360° circle on a plane normal to the axis of the implement 45.

As is well known in the fiber optics art, numerous functions can be accomplished through a waveguide such as fiber bundle 54. For example, substantially parallel but discrete bundles of fiber optics can be secured adjacent one another within the fiber bundle 54 to permit a plurality of discrete light transmitting channels. Alternatively, a plurality of concentric optical pathways can be provided as is well known in the art.

A plurality of discrete optical pathways may advantageously be used to perform a variety of functions. For example, a first optical pathway might be utilized to permit visualization of the stenotic site or other surface to be treated. A separate optical pathway may be utilized to transmit light for illuminating the site. Yet a third optical pathway might be utilized to transmit the laser light. These and other aspects of the fiber optics and laser light source are well known to those skilled in the fiber optics art.

A variety of additional functions may be performed through use of the additional interior space within the housing of steerable implement 45. For example, in a preferred embodiment, an aspiration duct may be provided near the distal end of the implement 45, for suctioning debris or gases which may be generated as a result of the action of the laser. Alternatively, in place of a waveguide 54, a flexible tube may be incorporated into the steering device of the present invention, thereby providing a working channel to receive additional implements therethrough.

Although this invention has been described in terms of certain preferred embodiments, other embodiments that are apparent to those of ordinary skill in the art are also within the scope of this invention. Accordingly, the scope of the invention is intended to be defined only by reference to the appended claims.

I claim:

1. A steerable guidewire for percutaneous transluminal insertion into the coronary vascular system and controlled negotiation of branches and turns therein, comprising:
   an axially elongate flexible housing having distal and proximate ends, said distal end being provided with a resilient tip;
   a flexible steering region displaced intermediate said distal and proximate ends of said housing; and
   at least one deflection wire for causing lateral deflection of said steering region upon axial displacement of said deflection wire along said housing.

2. The device of claim 1 wherein said steering region comprises a different material than the remainder of said body.

3. The device of claim 1, wherein said body comprises a wound coil.

4. The device of claim 3, wherein said coil has fewer revolutions per unit of axial distance along said body in said steering region.

5. The device of claim 1, wherein said body has a diameter less than 0.125 inches.

6. The device of claim 5, wherein said body has a diameter between 0.014 inches and 0.018 inches.

7. The device of claim 1, comprising at least three deflection wires.

8. A steering mechanism for a steerable guidewire having a flexible steering region, comprising:
   a steering post secured to said steering region in a manner that substantially prevents axial displacement thereof yet permits lateral deflection of the axis of said steering post away from the axis of said steerable guidewire;
   at least one deflection wire secured to said steering post; and
   a control device for axially displacing said deflection wires so as to laterally displace said steering post and said steering region.

9. The steering mechanism of claim 8, wherein said steering post has proximal and distal ends and wherein said deflection wire has proximal and distal ends and the distal end of said deflection wire is secured at a point intermediate said proximal and distal ends of said steering post.

10. The steering mechanism of claim 8, wherein said control device comprises a pivotably mountable circular plate secured to said deflection wires.

11. The steering mechanism of claim 8, wherein said control device comprises a single lever secured to said deflection wires, said lever being displaceable to any position throughout a nearly hemispherical range of motion.

12. The steering mechanism of claim 8, wherein said control device is provided with a stop to prevent bending of said steering post or said guidewire beyond their elastic limits.

13. A method of steering a guidewire of the type having at least one deflection wire for steering said guidewire and an elongate flexible shaft with a proximal and a distal end, said distal end being provided with a tip, through branches and turns in the coronary vascular system, comprising:
   introducing said guidewire into the coronary vascular system;

advancing said guidewire through the coronary vascular system until a branch or a turn is encountered;

steering said tip of said guidewire into said turn by axial displacement of said deflection wires and advancing said guidewire through said turn;

straightening said guidewire by axial displacement of said deflection wire; and further advancing said guidewire through the coronary vascular system.

14. The method of claim 13, wherein said guidewire has more than one deflection wire and wherein the straightening step comprises axial displacement of a different deflection wire than the deflection wire axially displaced in the steering step.

15. The method of claim 13, wherein said guidewire has at least three deflection wires and wherein axial movement of any one of said deflection wires in a proximal direction causes lateral deflection of said tip and allows a full 360° range of motion about the axis of said flexible shaft.

16. A steerable guidewire, comprising:
an elongate flexible housing having a diameter less than 0.125 inches and having proximal and distal ends and a central lumen extending therebetween, the distal end of said housing being flexible in a lateral direction; and
at least two deflection wires extending along the housing for causing lateral deflection of said distal end of said housing.

17. A steerable guidewire as in claim 16, additionally comprising a resilient tip on the distal end of said housing, said tip being movable between a first position on the axis of said housing and a second position displaced radially from the axis of said housing.

18. A steerable guidewire as in claim 16, wherein said housing has a diameter between 0.014 inches and 0.018 inches.

19. A steerable device for controlled negotiation through branches and turns, comprising:
an axially elongate body having distal and proximal ends and a central lumen therebetween;
a flexible steering region disposed intermediate said distal and proximal ends of said body;
a deflecting means within said central lumen; and
at least one deflection wire secured to said deflecting means for causing deflection of said steering region upon axial displacement of said deflection wire.

20. A guidewire as in claim 19, wherein there are at least three deflection wires so that through combinations of axial displacement of said deflection wires, said steering region is caused to deflect laterally and rotate throughout a full 360° range of motion about the axis of said flexible shaft.

21. A guidewire as in claim 19, wherein said deflecting means is a steering post.

22. A guidewire as in claim 19, additionally comprising a support for said deflecting means wherein said deflecting means is in pivotable contact with said support.

* * * * *

UNITED STATES PATENT AND TRADEMARK OFFICE
CERTIFICATE OF CORRECTION

PATENT NO.    : 5,037,391

DATED         : August 6, 1991

INVENTOR(S)   : Hammerslag et al.

It is certified that error appears in the above-identified patent and that said Letters Patent is hereby corrected as shown below:

Column 4, line 5 "tubular body with" should read "tubular body 11 with";

Column 4, line 63 "the body without" should read "the body 11 without";

Column 5, line 1 "The body of" should read "The body 11 of";

Column 7, line 9 "axis of the body is" should read "axis of the body 11 is"; and Column 8, lines 8-9, "control comprises" should read "control 18 comprises".

Signed and Sealed this

Sixteenth Day of March, 1993

*Attest:*

STEPHEN G. KUNIN

*Attesting Officer*     Acting Commissioner of Patents and Trademarks